United States Patent [19]

Ruyle et al.

[11] 4,044,049
[45] Aug. 23, 1977

[54] PHENYL BENZOIC ACID COMPOUNDS

[75] Inventors: William V. Ruyle, Scotch Plains; Lewis H. Sarett, Princeton; Alexander R. Matzuk, Colonia, all of N.J.

[73] Assignee: Merck & Co., Inc., Rahway, N.J.

[21] Appl. No.: 187,833

[22] Filed: Oct. 8, 1971

Related U.S. Application Data

[60] Division of Ser. No. 699,017, Jan. 19, 1968, Pat. No. 3,681,445, which is a continuation-in-part of Ser. No. 577,819, Sept. 8, 1966, abandoned, which is a continuation-in-part of Ser. No. 420,823, Dec. 23, 1964, abandoned.

[51] Int. Cl.$^2$ .............................................. C07D 69/14
[52] U.S. Cl. .......................... 260/479 R; 260/293.77; 260/559 H; 260/559 S; 544/171; 544/174; 544/173

[58] Field of Search .......... 260/479 R, 559 S, 247.77, 260/293.77, 559 H

[56] References Cited

U.S. PATENT DOCUMENTS

| | | | |
|---|---|---|---|
| 2,729,678 | 1/1956 | Sahyun et al. | 260/559 S |
| 2,879,290 | 3/1959 | Tiffany | 260/479 R |

Primary Examiner—Lorraine A. Weinberger
Assistant Examiner—Jane T. Fan
Attorney, Agent, or Firm—William H. Nicholson; Frank M. Mahon; Raymond M. Speer

[57] ABSTRACT

The invention relates to substituted 5-(phenyl)benzoic acid esters and non-toxic pharmaceutically accepted salts thereof and processes for their preparation. The substituted 5-(phenyl)benozic acids are useful as anti-inflammatory compounds. Also included are method of treating inflammation claims by administering these particular compounds to patients.

5 Claims, No Drawings

PHENYL BENZOIC ACID COMPOUNDS

CROSS REFERENCES TO RELATED APPLICATIONS

This application is a division of prior co-pending application Ser. No. 699,017, filed Jan. 19, 1968, now U.S. Pat. No. 3,681,445, issued Aug. 1, 1972, which in turn is a continuation-in-part of application Ser. No. 577,819, filed Sept. 8, 1966, now abandoned, which in turn is a continuation-in-part of application Ser. No. 420,823, filed Dec. 23, 1964, now abandoned.

BACKGROUND OF INVENTION

1. Field of Invention

Generally, this invention relates to substituted 5-(phenyl)benzoic acids, esters and non-toxic pharmaceutically acceptable salts thereof for use in the treatment of inflammatory type disease. It is an object of this invention to prepare compounds having anti-inflammatory properties but not having many of the side effects which are generally associated with steroid type anti-inflammatory agents. Prior to this time, steroid type anti-inflammatory agents such as CORTONE, HYDROCORTONE and DECADRON were commonly used to relieve inflammation but as stated these compounds exhibit many undesirable side effects.

2. Description of the Prior Art

The closest prior art compounds which could be found are those shown and described in U.S. Pat. Nos. 2,744,916 and 3,123,543. Neither of these patents disclose an anti-inflammatory use for the compounds. These references disclose 2-hydroxy-5-phenyl benzoic acid (5-phenyl salicylic acid) and various ester and amide derivatives thereof. Also the prior art discloses acetyl salicylic acid (aspirin). The compounds of the instant invention, however, are more potent that the prior art compounds at lower dosages and exhibit fewer side effects than the prior art compounds. The prior art compounds disclosed in the two patent references are not substituted with halo or halo groups on the phenyl moiety attached to the 5-position of the benzoic acid.

SUMMARY OF THE INVENTION AND DESCRIPTION OF THE PEFERRED EMBODIMENTS

This invention relates to new biphenyl compounds, and to a method of treating inflammation using these compounds and to processes for producing the same. More specifically, this invention relates to substituted 5-(phenyl)benzoic acids, esters, amides, anhydrides and non-toxic pharmaceutically acceptable salts thereof. Still more specifically, this invention relates to compounds having the following general formula:

I

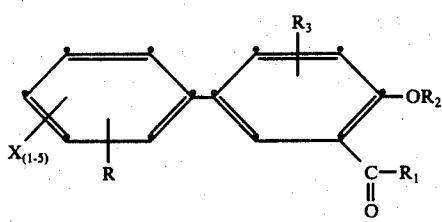

wherein:

$X_{(1-5)}$ is halogen (chloro, bromo, fluoro and iodo), X being on one or more of the phenyl carbon atoms;

R is selected from the group consisting of hydrogen, halogen (chloro, bromo, and fluoro), lower alkyl (such as methyl, ethyl, butyl, pentyl, and the like), and lower alkoxy (such as methoxy, ethoxy, butoxy, and the like);

$R_1$ is selected from the group consisting of hydroxy, amino, lower alkoxy (such as methoxy, ethoxy, butoxy, pentoxy, and the like), lower alkylamino (methylamino, propylamino, pentylamino, and the like), di(lower alkyl)amino (dimethylamino, dibutylamino, propylpentylamino, and the like), diloweralkylaminoloweralkylamino, diloweralkylaminoloweralkoxy, hydroxyloweralkoxy, (3-hydroxypropoxy, 2-hydroxypropoxy, 4-hydroxybutoxy and the like), polyhydroxyloweralkoxy (2,3-dihydroxypropoxy, 2,3,4,5,6-pentahydroxyhexyloxy and the like), loweralkoxyloweralkoxy (ethoxyethoxy), phenyl-loweralkoxy (benzyloxy, phenethoxy and the like), phenoxy, substituted phenoxy (such as loweralkanoylamino, benzyloxy-2-carboxy-4-(4'-fluorophenyl), carboxy and carbloweralkoxy, loweralkanoylamino-loweralkoxy, hydrazino, (hydroxylamino), N-morpholino, N-(4-loweralkyl-piperidino)N-[4-(hydroxyloweralkyl)-piperidino], (hydroxyloweralkyl)amino and a naturally occurring amino acid radical with attachment at the N, such as glycine, phenylalanine, proline, methionine and taurine;

$R_2$ is selected from the group consisting of hydrogen, lower alkyl (such as methyl, ethyl, butyl, pentyl, and the like), lower alkanoyl (such as acetyl, propionyl, butyryl, and the like), and lower alkenyl (such as allyl, butenyl, and the like);

$R_3$ is selected from the group consisting of hydrogen, 3-lower alkenyl, 3- and 4-lower alkyl, lower alkoxy, benzyl and halo; the pharmaceutically non-toxic salts of the acid [(such as the ammonium, alkali (Na,K) and alkali earth (Ca,Ba,Mg), amine, aluminum, iron, choline, glucosamine, and S-methyl methionine salts, piperazine, diloweralkylaminoloweralkanol, chloroquine, hydroxychloroquine and the like]; the anhydride of said acids and the mixed anhydrides of said acids and 2-acetoxy benzoic acid, provided that when R is hydrogen or halo;

$R_1$ cannot be hydroxy, phenoxy, diloweralkylamino or diloweralkylamino lower alkoxy;

$R_2$ is hydrogen or lower alkanoyl; and $R_3$ is hydrogen or methyl.

In the more preferred aspects of this invention,

R is hydrogen or lower alkyl, particularly methyl or lower alkoxy, particularly methoxy;

$R_1$ is hydroxy or amino, particularly hydroxy;

$R_2$ is hydrogen or lower alkanoyl, particularly acetyl;

$R_3$ is hydrogen or lower alkyl;

X is chloro or fluoro particularly fluoro and is on the 4-position of the phenyl moiety; provided that $R_1$ cannot be hydroxy when R is hydrogen and $R_3$ is hydrogen or methyl.

Representative compounds of this invention are:

2-hydroxy-5-(4'-fluorophenyl)-benzamide;
2-hydroxy-5-(4'-fluorophenyl)-3-methyl benzamide;
2-acetoxy-5-(4'-fluorophenyl)-benzamide;
2-acetoxy-5-(4'-fluorophenyl)-benzmorpholide;
2-hydroxy-5-(4'-fluoro-2'-methoxyphenyl)benzoic acid;

2-acetoxy-5-(4'-fluoro-2'-methoxyphenyl)benzoic acid;
2-hydroxy-5-(4'-fluoro-2'-methylphenyl)benzoic acid;
2-acetoxy-5-(4'-fluoro-3'-methylphenyl)benzoic acid;
2-hydroxy-3-allyl-5-(4'-fluorophenyl)benzoic acid; and
2-hydroxy-3-propyl-5-(4'-fluorophenyl)benzoic acid.

This invention also relates to a method of treating inflammation in patients using a compound of Formula I, particularly an especially preferred compound as the active constituent.

We have found that the compounds of Formula I have anti-inflammatory activity and are effective in the prevention and inhibition of edema and granuloma tissue formation as shown by reduction of edema in the rat's foot induced by the injection of an inflammatory (phlogistic) agent into the rat's foot.

The compounds of the instant invention can be used to treat inflammation by reducing inflammation and relieving pain in such diseases as rheumatoid arthritis, osteoarthritis, gout, infectious arthritis and rheumatic fever. Furthermore, the compounds of the instant invention have better potency at the same dosage levels than similar type compounds known in the prior art and exhibit a lower incidence of side effects.

The compounds of Formula I also have antipyretic and analgesic activity and would be administered and used in the same manner and in the same dosage ranges as if they were being used to treat inflammation as discussed further on.

The treatment of inflammation in accordance with the method of the present invention is accomplished by orally administering to patients a composition of a compound of Formula I, particularly the especially preferred compounds in a non-toxic pharmaceutically acceptable carrier, preferably in tablet or capsule form.

The non-toxic pharmaceutical carrier may be, for example, either a solid or a liquid. Exemplary of solid carriers are lactose, corn starch, gelatin, talc, sterotix, stearic acid, magnesium stearate, terra alba, sucrose, agar, pectin, cab-o-sil, and acacia. Exemplary of liquid carriers are peanut oil, olive oil, sesame oil and water. Similarly, the carrier or diluent may include a time delay material such as glyceryl monostearate or glyceryl distearate alone or with a wax.

Several pharmaceutical forms of the therapeutically useful compositions can be used. For example, if a solid carrier is used, the compositions may take the form of tablets, capsules, powders, troches or lozenges, prepared by standard pharmaceutical techniques. If a liquid carrier is used, the preparation may be in the form of a soft gelatin capsule, a syrup or a liquid suspension.

The active compounds of Formula I and of the compositions of this invention are present in an amount sufficient to treat inflammation, that is to reduce inflammation. Advantageously, the composition will contain the active ingredient, namely, the compounds of Formula I in an amount of from about 1 mg. to 140 mg. per kg. body weight per day (50 mg. to 10 g. per patient per day), preferably from about 2 mg. to 70 mg./kg. body weight per day (100 mg. to 5 g. per patient per day).

The method of treatment of this invention comprises internally administering to a patient (animal or human), a compound of Formula I, particularly an especially preferred compound admixed with a non-toxic pharmaceutical carrier such as exemplified above. The compounds of Formula I and particularly the especially preferred compounds will be present in an amount of from 1 mg. to 140 mg./kg. body weight per day, preferably from about 2 mg. to about 70 mg. per kilogram body weight per day and espcially from 4 mg. to 10 mg./kg. body weight per day. The most rapid and effective anti-inflammatory effect is obtained from oral administration of a daily dosage of from about 4 to 10 mg./kg./day. It should be understood, however, that although preferred dosage ranges are given, the dose level for any particular patient depends upon the activity of the specific compound employed. Also many other factors that modify the actions of drugs will be taken into account by those skilled in the art in the therapeutic use of medicinal agents, particularly those of Formula I, for example, age, body weight, sex, time of administration, route of administration, rate of excretion, drug combination, reaction sensitivities and severity of the particular disease.

The test method by which anti-inflammatory activity is determined is by the ability of the compounds of Formula I to inhibit the edema induced by injection of an inflammatory (phlogistic) agent into the tissue of the foot of the rat. Groups of six male rats (Sprague Dawley strain, 150 ± 15 g.) each are given orally the compounds to be tested one hour before 0.1 ml. of 1% suspension of carragenin is injected into the plantar surface of the right hind paw. Immediately and again three hours later the foot volume is measured by its placement of mercury and recorded automatically. The difference between the immersion and final volumes is a measurement of the edema produced. The compounds tested were suspended or dissolved in 0.5% methocel whereas controls received only the methocel. A usual test of 30 mg./kg. and one repetition plus one dose of 90 mg./kg. were usually given.

The above test method is known to correlate with anti-inflammatory activity in humans and is a standard test used to determine anti-inflammatory activity. This correlation is shown by compounds known to be clinically active, including, INDOCIN, ASPIRIN, BUTAZOLIDIN, TANDEARIL, CORTON, HYDROCORTONE and DECADRON.

The compounds of this invention may be prepared either from a biphenyl phenol or from the following type starting material:

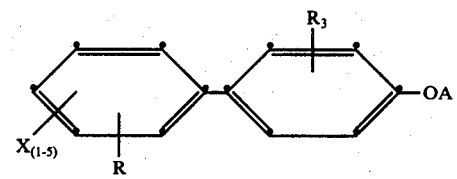

wherein:
A is an alkali metal ion; and
X, $R_3$ and R are as previously defined.

Some of these compounds are prepared from the individual phenyl moieties of the above starting material by the well-known Gomberg reaction. Others, where the biphenyl moiety is known, require the appropriate reactions to obtain the functional group, if needed, as well as the metal salts. However, all of the compounds may be obtained by first preparing an aniline compound containing an X and, if desired, an R group, followed by a Gomberg reaction with nitrobenzene or anisole or an $R_3$ substitued nitrobenzene or anisole, subsequently reacting either the nitro group or the methoxy group (from nitrobenzene or anisole) of the biphenyl compound thus prepared so as to obtain the alkali salt starting material. For example, 2-fluoro-5-nitroaniline may be diazotized to the corresponding 2-fluoro-5-nitrophenol which in turn may be alkylted to form the corresponding 3-alkoxy-4-fluoronitrobenzene, and finally reducing the nitro group to obtain the appropriate aniline compound needed for the Gomberg reaction. (When as in this cited example, the benzene compound contains an alkoxy group, the Gomberg reaction is carried out with nitrobenzene.) The methoxy substituted aniline compound is then reacted with nitrobenzene in the presence of isoamyl nitrite. The nitrobiphenyl compound thus obtained may be readily reduced to the amino compound and subsequently diazotized to the corresponding hydroxy compound. Alternatively, when the aniline compound used in the Gomberg reaction does not have an alkoxy substituent on it, it may be reacted with an alkoxy benzene rather than nitrobenzene. Using this procedure, the alkoxy biphenyl compound obtained after the Gomberg reaction may, by one step, be converted to the corresponding hydroxybiphenyl compound, for example, by reaction with hydriodic acid.

Although the above reaction sequence can be used when $R_3$ is methyl, it is preferred to carry out the following reaction sequence when $R_3$ is lower alkyl: For example, the methyl-2-hydroxy-5-(4'-fluorophenyl)-benzoate compound of this invention is reduced to the corresponding alcohol. This alcohol compound is then acylated, whereupon it is subsequently hydrogenated to the corresponding 4-(4'-fluorophenyl)-2-methylphenyl acetate. This compound is then saponified or hydrolyzed to the corresponding phenol compound, which in turn is carbonated to form the (5-(4'-fluorophenyl)-2-hydroxy-3-methylbenzoic acid. Further, when $R_3$ is to be a lower alkenyl group, the following procedure is preferred: For example, methyl 5-(4'-fluorophenyl)-2-hydroxy benzoate is heated with potassium carbonate in acetone to form the corresponding 2-allyloxy compound. This product is then heated at high temperatures to cause a rearrangement to the corresonding 3-allyl-2-hydroxy compound. Further, an additional method for preparing an $R_3$ alkyl is by reduction, for example, of the above-noted 3-allyl compound to the corresponding 3-propyl compound. In addition, the 3-allyl compound above may be heated with potassium hydroxide to obtain a double bond shift to form the 3-propenyl compound.

In the Gomberg reaction mentioned above, a mixture of isomers of the biphenyl compound is obtained; therefore, in order to obtain the desired 4-(substituted phenyl)-benzene compound in a pure form a chromatographic separation is required.

The 4-(substituted phenyl)-phenol compounds obtained as described above may then be converted to the corresponding alkali salt by any well-known means, for example, reaction with an appropriate alkali metal in an inert solvent.

The acid compounds of this invention may be prepared from the previously prepared alkali phenolate or phenol compound. The preparation of these acid compounds are carried out by using the well-known Kolbe-Schmidt carbonation procedure. In this carbonation step, the phenolate is reacted with carbon dioxide or the phenol is reacted with carbon dioxide in the presence of an alkali carbonate. Many of the acids which are not claimed in this invention can be used as starting materials for the novel esters and amides of this invention. The process may be shown as follows:

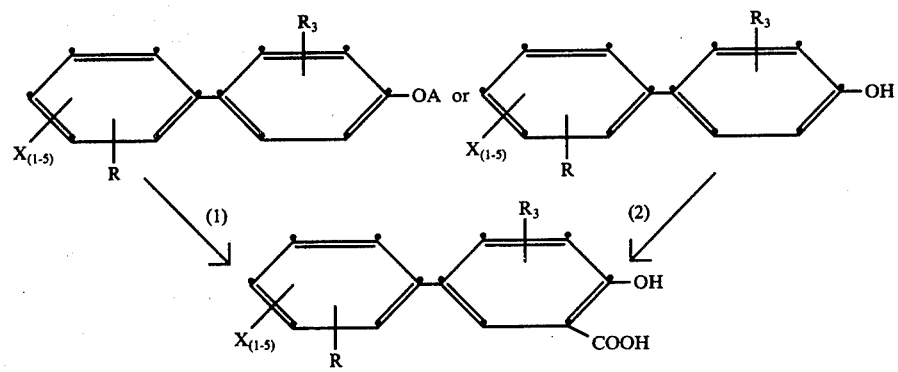

Euivalents: As previously indicated,
Reactions and Conditions:

Step 1. Reaction with carbon dioxide at elevated temperatures (above 75° C. preferably above 100° C.) with or without a solvent preferably without a solvent (or if the solvent is used, any high-boiling inert solvent may be used) until the reaction is substantially complete; and subsequent acidification of the reaction mixture.

Step 2. Reaction with carbon dioxide in the presence of an alkali carbonate, such as potassium, sodium, and the like, especially potassium, at elevated temperatures (above 75° C. preferably above 100° C.) with or without a solvent preferably without a solvent (or if the solvent is used, any high-boiling inert solvent may be used) until the reaction is substantially complete; and subsequent acidification of the reaction mixture.

Reaction steps (1) and (2) are the well-known Kolbe-Schmidt reaction. Since the reaction conditions are not critical, this invention contemplates not only the particular procedure shown but all other variations of this carbonation step which are well-known in the art.

The compounds of this invention, wherein $R_1$ is a group such that an ester is the final compound, (i.e. $R_1$ = alkoxy), are prepared by any esterification procedure, using an esterifying agent containing the appropriate $R_1$ group. For example, the benzoic acid compounds of this invention may be reacted with the appropriate lower alkanol (preferably methanol) at elevated temperatures in the presence of a strong acid, such as hydrochloric acid, sulfuric acid, p-toluenesulfonic acid, and the like, to form the desired $R_1$ compound.

The compounds of this invention wherein $R_1$ is a group such that an amide is the final compound (i.e., $R_1$ is amino), may be prepared by any suitable amidation reaction. For example, the benzoic acid compound (preferably the methyl or ethyl ester) may be reacted with ammonia, ammonium hyroxide, or an amine compound, at any suitable temperature (room temperature to reflux). When the amino group is desired, it is preferred to carry out the reaction with ammonia in a bomb at temperatures above 100° C. to form the desired $R_1$ (amino) compound. Preferably, when an amide is desired which is derived from an amino acid, the following reaction sequence is followed: The benzoic acid final compound is reacted with isobutyl chlorocarbonate to form the mixed anhydride. This compound is in turn reacted with the desired amino acid ester and subsequently hydrolyzed to form the desired amide.

The final compound, wherein $R_2$ is lower alkanoyl (preferably acetyl), may be prepared by any suitable alkanoylation reaction. For example, the corresponding hydroxy benzoic acid, ester, or amide (preferably the ester), may be reacted with a lower alkanoic acid anhydride (preferably acetic anhydride) in the presence of a catalyst, such as sulfuric acid, pyridine, p-toluenesulfonic acid, and the like (preferably pyridine), at any suitable temperature (room temperature to elevated temperatures) preferably at elevated temperatures to form the desired $R_2$ compound.

The final compound, wherein $R_2$ is lower alkyl (preferably methyl), may be prepared by any appropriate alkylation reaction. For example, the corresponding hydroxy benzoic acid, ester, or amide (preferably the ester), may be reacted with a di(lower alkyl) sulfate (preferably dimethyl sulfate) in the presence of a base (such as an alkali carbonate) at any suitable temperature (room temperature to reflux but preferably at or near reflux) with subsequent acidification of the reaction mixture, such as with hydrochloric acid, sulfuric acid, and the like, to form the desired $R_2$ compound.

The final Compound, wherein $R_2$ is a lower alkenyl (preferably allyl), may also be prepared by any appropriate alkylation reaction. For example, the hydroxy benzoic acid, ester, or amide (preferably the ester), may be reacted with an alkenyl halide in the presence of a base containing an inorganic cation, such as sodium methoxide, potassium ethoxide, sodium carbonate, and the like, in an inert solvent which affords at least some solubilization [such as dioxane, tetrafuran, lower alkanol, dimethoxy ethane, acetone, and the like (preferably a lower alkanol, such an methanol)] at any suitable temperature (room temperature to elevated temperatures, preferably at elevated temperatures) to form the desired $R_2$ compound.

The salts of the final acid compounds of this invention may be prepared by any of the well-known methathesis procedures. For example, the benzoic acid compound may be reacted with an inorganic base, such as sodium hydroxide, potassium hydroxide, ammonium hydroxide, barium hydroxide, and the like. The anhydrides of this invention may be prepared by any of the well-known procedures in the art.

The preparation of these compounds containing the $R_1$ and $R_2$ groups other than hydrogen may be prepared in any order. The $R_1$ group could be placed on the molecule followed by addition of the $R_2$ substituent or by first obtaining the $R_2$ compound followed by addition of the $R_1$ group. The order of these reactions is not critical; they can be run in any desired fashion:

The following examples are used by way of illustration:

EXAMPLE 1

4-Fluoro-3-methoxyaniline

A. 2-Fluoro-5-nitrophenol

A solution of 3.2 grams of 2-fluoro-5-nitroaniline, sulfuric acid (3 cc., d 1.84) and 8 ml. of water is stirred into a solution of 1.5 grams of sodium nitrite in water, maintained below 5° C. After 10 minutes, the excess nitrous acid is destroyed by urea, the reaction mixture filtered, and the filtrate added to 40 ml. of boiling 50% sulfuric acid. After complete addition, the mixture is boiled an additional 15 minutes, cooled, and the separated phenol filtered and washed with water. It is then purified by recrystallization from hexane.

B. 2-Fluoro-5-nitroanisole

An intimate mixture of 2.0 grams of 2-fluoro-5-nitrophenol, 2.0 grams of potassium carbonate, and 1.0 ml. of methyl sulphate, is heated on the steam bath for 5 minutes and then steam distilled, the volume of liquid in the flask being kept as small as possible. The 2-fluoro-5nitroanisole passes over, and a further quantity is obtained by adding more potassium carbonate (1 gram) and methyl sulphate (0.5 ml.) to the residual liquor, which is then warmed and steam distilled. The 2-fluoro-5-nitroanisole is then recrystallized from hexane.

C. 4-Fluoro-3-methoxyaniline

A suspension of 10 grams of 2-fluoro-5-nitroanisole and 100 ml. of dioxane is reduced catalytically under 40 p.s.i. of hydrogen and 1.0 gram of 5% Pd/C. After the uptake of hydrogen ceases, the catalyst is filtered, and the filtrate is concentrated in vacuo to yield 4-fluoro-3-methoxyaniline.

Alternatively, the compound may be prepared as follows:

A. 2-Fluoro-5-nitroanisole

To a stirred solution of 35 ml. concentrated hydrochloric acid and 40 ml. water is added 48 grams of 2-amino-5-nitroanisole. The mixture is warmed and then cooled to 0°-5° C. To the stirred mixture is added dropwise 20 grams sodium nitrite in 120 ml. water maintaining the temperature at 0° – 5° C. After addition is complete the reaction mixture is filtered and cooled with stirring while 70 ml. fluoboric acid (48%) is added. The homogeneous solution is allowed to stir in the cold for an additional hour during which time a yellow precipitate forms. The precipitate is filtered, washed with cold water, ethanol and ether and air dried to yield 31.4 grams of the diazonium fluoborate.

A mixture of 21.4 grams diazonium fluoborate and 60 grams sand is stirred wile heating in an oil bath. When the evolution of gases commences, the bath is lowered. After the reaction slows down, the bath is applied again. This prodedure is repeated until evolution of gases has ceased. The reaction mixture is then heated at 200° C. for an additional one-half hour. After cooling to room temperature, the residue is extracted with chloroform. The extract is evaporated in vacuo and the residue subjected to a steam distillation. A white solid is formed in the distillate. The solid is extracted with ether, which is removed to yield 2.6 grams of the 2-fluoro-5-nitroanisole. A sample is recrystallized from ethanol to give a pure product with a melting point of 69° – 71° C.

Calculated for $C_7H_6FNO_3$: C, 49.13; H, 3.53; N, 819; F, 11.10. Found: C, 49.33; H, 3.60; N, 8.17; F, 10.96.

B. 4-Fluoro-3-methoxyaniline

A solution of 5.4 grams 2-fluoro-5-nitroanisole in 125 ml. methanol is reduced by hydrogen at room temperature and 40 p.s.i. pressure using 100 mg. platinum oxide catalyst. After the required uptake of hydrogen, the mixture is filtered, 50 ml. 2.5 N hydrochloric acid added and the resulting solution is evaporated in vacuo. After washing the residue with ether, it is dissolved in methanol, filtered and diluted with excess ether. The precipitate is filtered, washed with ether and dried in vacuo at room temperature. The 4-fluoro-3-methoxyaniline hydrochloride darkens at 250° C. and melts 260° – 265° C.

Calculated for $C_7H_8FNO.HCl$: C, 47.33; H, 5.11; N, 7.89; F, 10.70; Cl, 19.96. Found: C, 47.35; H, 5.14; N, 7.66; F, 10.9; Cl, 20.05.

When 4'-fluoro-4-nitrobiphenyl is used in place of 2-fluoro-nitroanisole in part C of the above example, there is obtained 4-(4'-fluorophenyl)-aniline.

EXAMPLE 2

4'-Fluoro-2'-methoxy-4-nitrobiphenyl

A mixture of 7.7 grams of 4-fluoro-2-methoxyaniline, 200 ml. of nitrobenzene, and 9.0 grams of isoamyl nitrite, is warmed on the steam bath until a vigorous reaction with evolution of gas sets in. This evolution is allowed to proceed without heating until it has subsided, and the mixture is then heated on the steam bath for an additional 3 hours. The excess of nitrobenzene is removed in vacuo. The residue is purified for the desired isomer by elution from a silica gel column using petroleum-benzin to yield 4'-fluoro-2'-methoxy-4-nitrobiphenyl.

When pentafluoroaniline, 2-fluoroaniline or 4-fluoro-3-methoxyaniline (obtained from Example 1) is used in place of 4-fluoro-2-methoxyaniline in the above example, there is obtained 2', 3', 4', 5', 6'-pentafluoro-4-nitrobiphenyl, 2'-fluoro-4-nitrobiphenyl or 4'-fluoro-3'-methoxy-4-nitrobiphenyl respectively.

When 2-nitrotoluene, 2-ethyl-nitrobenzene, 2-methoxy-nitrobenzene, 2-ethoxy-nitrobenzene, 2-chloro-nitrobenzene, 2-bromo-nitrobenzene, 3-nitrotoluene, 3-ethylnitrobenzene, 3-methoxy-nitrobenzene, 3-ethoxy-nitrobenzene, 3-chloro-nitrobenzene, or 3-bromo-nitro-benzene are used in place of nitrobenzene in the above example, there is obtained the corresponding 2- and 3-alkyl, halo or alkoxy biphenyls.

When 4-fluoroaniline and 2-methyl-nitrobenzene are used in the above example in place of 4-fluoro-2-methoxyaniline and nitrobenzene there is obtained 4'-fluoro-3-methyl-4-nitrobiphenyl.

EXAMPLE 3

4-(4'-Fluoro-2'-methoxyphenyl)-aniline

A mixture of 10 grams of 4'-fluoro-2'-methoxy-4-nitrobiphenyl in 250 ml. of ethanol is reduced by hydrogen at atmospheric pressure and at room temperature using 5% palladium-on-charcoal (0.5 gram) catalyst. After the required uptake of hydrogen, the mixture is filtered and the catalyst washed with fresh ethanol. The ethanol solution is then concentrated in vacuo, and the residue recrystallized from aqueous ethanol to yield 4-(4'-fluoro-2'-methoxyphenyl)-aniline.

When b 2', 3', 4', 5', 6'-pentafluoro-4-nitrobiphenyl, 2'-fluoro-4-nitrobiphenyl or 4'-fluoro-3'-methoxy-4-nitrobiphenyl obtained from Example 2 are used in place of 4'-fluoro-2'-methoxy-4-nitrobiphenyl in the above example, there is obtained 4-(pentafluorophenyl)-aniline, 4-(2'-fluorophenyl)-aniline or 4-(4'-fluoro-3'-methoxyphenyl)-aniline.

When the 2- and 3-alkyl, halo or alkoxy biphenyls obtained from Example 2 are used in place of 4'-fluoro-2-methoxy-4-nitrobiphenyl in the above example, there are obtained the corresponding 2- or 3-alkyl, halo or alkoxy aniline compounds.

Similarly, when 4'-fluoro-3-methyl-4-nitrobiphenyl obtained from Example 2 is used in place of 4'-fluoro-2'-methoxy-4-nitrobiphenyl in the above example, there is obtained 2-methyl-4-(4'-fluorophenyl)-aniline.

EXAMPLE 4

4-(4'-Fluoro-2'-methylphenyl)-anisole

A mixture of 9.0 grams of 4-fluoro-2-methyl-aniline, 200 ml. of anisole, and 9.0 grams of iso-amyl-nitrate, is warmed on a steam bath until a vigorous reaction with evolution of gas sets in. This evolution is allowed to proceed without heating until it has subsided, and the mixture is then heated on the steam bath for an additional 3 hours. The excess anisole is removed in vacuo, and the residue is chromatographed on a silica gel column using petroleum-benzin as eluent to yield 4-(2'-methyl-4'-fluorophenyl)-anisole.

When 2-chloro-4-fluoroaniline, 4-fluoro-3-methylaniline, 2,4-difluoroaniline, 3-fluoroaniline and 4-fluoro-3-chloroaniline are used in place of 2-methyl-4-fluoroaniline in the above example, there are obtained the corresponding 4-(2'-chloro-4'-fluorophenyl)-anisole, 4-(4'-fluoro-3'-methylphenyl)-anisole, 4-(2',4'-difluoro-phenyl)-anisole, 4-(2',4'-difluoro-phenyl)-anisole, 4-(3'-fluorophenyl)-anisole and 4-(4'-fluoro-3'-chloro-phenyl)-anisole.

When 2-methylanisole, 2-ethylanisole, 2-benzylanisole, 3-methylanisole, 3-ethylanisole, 3-benzylanisole, 2-chloroanisole, 2-bromoanisole, 3-chloroanisole or 3-bromoanisole is used in place of anisole in the above example, there is obtained the corresponding 2- or 3-alkyl, benzyl or halo phenyl-anisole compound.

EXAMPLE 5

4-(2'-Methyl-4'-fluorophenyl)-phenol

To a solution of 2.1 grams of 4-(2'-methyl-4'-fluorophenyl)-anisole in 50 ml. of boiling acetic acid is added 5 ml. of hydriodic acid and the boiling continued for 3 hours. Water is added and the reaction mixture cooled and the 4-(2'-methyl-4'-fluorophenyl)-phenol crystallizes. Further purification is then achieved by recrystallization of the solid from aqueous ethanol to yield 4-(2'-methyl-4'-fluorophenyl)-phenol.

When 4-(2'-chloro-4'-fluorophenyl)-anisole, 4-(4'-fluoro-3'-methylphenyl)-anisole, 4-(2',4'-difluorophenyl)-anisole, 4-(3'-fluorophenyl)-anisole and 4-(4'-fluoro-3'-chlorophenyl)-anisole obtained from Example 4 are used in place of 4-(2'-methyl-4'-fluorophenyl)-anisole in the above example, there are obtained the corresponding 4-(2'-chloro-4'-fluorophenyl)-phenol, 4-(4'-fluoro-3'-methylphenyl)-phenol, 4-(2',4'-difluorophenyl)-phenol, 4-(3'-fluorophenyl)-phenol and 4-(4'-fluoro-3'-chlorophenyl)-phenol.

When the 2- or 3-alkyl, benzyl or halo phenylanisole compounds obtained from Example 4 above are used in place of 4-(3'-methyl-4'-fluorophenyl)-anisole in the above example, there is obtained the corresponding 4-(substituted phenyl)-2- or 3-alkyl, benzyl or halo phenol compound.

EXAMPLE 6

4-(4'-Fluoro-2'-methoxyphenyl)-phenol

A solution of 32.00 grams of 4-(4'-fluoro-2'-methoxyphenyl)-aniline in 120 ml. of glacial acetic acid is cooled to 10° – 12° C. To this solution is added slowly a solution of 12.25 grams of sodium nitrite in 120 ml. of water with stirring and continued cooling. Five minutes after this addition, the suspension of the diazonium acetate is added slowly to a boiling solution of 100 ml. of concentrated sulfuric acid and 200 ml. of water. After the final addition of the diazonium salt, the suspension is boiled for an additional 5 minutes and then allowed to cool to room temperature. The reaction mixture is then filtered and the cake dried in vacuo to yield 4-(4'-fluoro-2'-methoxyphenyl)-phenol.

When 4-(2'-fluorophenyl)-aniline, 4-(pentafluorophenyl)-aniline, 4-(4'-fluorophenyl)-aniline, and 4-(4'-fluoro-3'-methoxyphenyl)-aniline, obtained from Example 3 are used in place of 4-(4'-fluoro-2'-methoxyphenyl)-aniline in the above example, there are obtained the corresponding 4-(2'-fluorophenyl)-phenol, 4-(pentafluorophenyl)-phenol, 4-(4-(4'-fluorophenyl)-phenol, and 4-(4'-fluoro-3'-methoxyphenyl)-phenol.

When the alkyl, halo or alkoxy aniline compounds obtained from Example 3 are used in place of 4-(4'-fluorophenyl)-aniline in the above example, there is obtained the corresponding 2- or 3-alkyl, halo or alkoxy phenol compound.

Similarly, when 2-methyl-4-(4'-fluorophenyl)-aniline obtained from Example 3 is used in place of 4-(4'-fluorophenyl)-aniline in the above example, there is obtained 2-methyl-4-(4'-fluorophenyl)-phenol.

EXAMPLE 7

2-Hydroxy-5-(4'-fluoro-2'-methoxyphenyl)-benzoic acid

A mixture of 10 grams of 4-(4'-fluoro-2'-methoxyphenyl)-phenol and 27.2 grams of potassium carbonate is exposed to carbon dioxide at 1300 p.s.i. and 175° C. The dark mass obtained from this carbonation is then dissolved in 300 ml. of water and 200 ml. of methylene chloride and the two layers separated. The water layer is then extracted with 100 ml. of methylene chloride and then acidified with 2.5 normal hydrochloric acid. This mixture is then filtered and the cake dried in vacuo to yield 5.32 grams of the crude product. The crude product is then recrystallized from benzenemethanol to yield 2.7 grams of material. An additional crystallization of this semi-pure material from benzenemethanol yields analytically pure 2-hydroxy-5-(4'-fluoro-2'-methoxyphenyl)-benzoic acid (m.p. 205°–207° C.).

When 4-(2'-methyl-4'-fluorophenyl)-phenol, 4-(2'-chloro-4'-fluorophenyl)-phenol, 4-(4'-fluoro-3'-methylphenyl)-phenol, 4-(2',4'-difluorophenyl)-phenol, 4-(3'-fluorophenyl)-phenol, and 4-(4'-fluoro-3'-chlorophenyl)-phenol, obtained from Example 5 and 4-(2'-fluorophenyl)-phenol, 4-(pentafluorophenyl)-phenol, 4-(4'-fluorophenyl)-phenol, and 4-(4'-fluoro-3'-methoxyphenyl)phenol, obtained from Example 6 are used in place of 4-(4'-2'-methoxyphenyl)-phenol in the above example, there are obtained the corresponding 2-hydroxy-5-(2'-methyl-4'-fluorophenyl)-benzoic acid (m.p. 175° – 177° C.), 2-hydroxy-5-(2'-chloro-4'-fluorophenyl)-benzoic acid, 2-hydroxy-5-(4'-fluoro-3'-methylphenyl)-benzoic acid (m.p. 208 - 209° C.), 2-hydroxy-5-(2',4'-difluorophenyl)-benzoic acid (m.p. 210 - 211° C.), 2-hydroxy-5-(3'-fluorophenyl)-benzoic acid (m.p. 196° – 197° C.), 2-hydroxy-5-(4'-fluoro-3'-chlorophenyl)-benzoic acid, 2-hydroxy-5-(2'-fluorophenyl)-benzoic acid (m.p. 201° – 203° C.), 2-hydroxy-5-(pentafluorophenyl)-benzoic acid (m.p. 241° – 243° C.), 2-hydroxy-5-(4'-fluorophenyl)-benzoic acid (m.p. 199° – 203° C.), and 2-hydroxy-5-(4'-fluoro-3'-methoxyphenyl)-benzoic acid (m.p. 206°–208° C.).

When the 4-(substituted-phenyl) 2- or 3-alkyl, benzyl or halo phenol compounds of Example 5 or the 2- or 3-alkyl, halo or alkoxy phenol compounds of Example 6 are used in place of 4-(4'-fluoro-2'-methoxyphenyl)-phenol in the above, there are obtained 2-hydroxy-3-methyl-5-(4'-fluoro-2'-methoxyphenyl)-benzoic acid, 2-hydroxy-3-ethyl-5-(4'-fluoro-2'-methoxyphenyl)-benzoic acid, 2-hydroxy-3-methoxy-5-(4'-fluoro-2'-methoxyphenyl)-benzoic acid, 2-hydroxy-3-ethoxy-5-(4'-fluoro-2'- methoxyphenyl)-benzoic acid, 2-hydroxy-3-chloro-5-(4'-fluoro-2'-methoxyphenyl)-benzoic acid, 2-hydroxy-3-bromo-5-(4'-fluoro-2'-methoxyphenyl)-benzoic acid, 2-hydroxy-4-methyl-5-(4'-fluoro-2'-methoxyphenyl)-benzoic acid, 2-hydroxy-4-ethyl-5-(4'-fluoro-2'-methoxyphenyl)-benzoic acid, 2-hydroxy-4-methoxy-5-(4'-fluoro-2'-methoxyphenyl)-benzoic acid, 2-hydroxy-4-ethoxy-5(4'-fluoro-2'-methoxyphenyl)-benzoic acid, 2-hydroxy-4-chloro-5-(4'-fluoro-2'-methoxyphenyl)-benzoic acid, 2-hydroxy-4-bromo-5-(4'-fluoro-2'-methoxyphenyl)-benzoic acid, 2-hydroxy-3-methyl-5-(3'-chloro-4'-fluorophenyl)-benzoic acid, 2-hydroxy-3-ethyl-5-(3'-chloro-4'-fluorophenyl)-benzoic acid, 2-hydroxy-3-benzyl-5-(3'-chloro-4'-fluorophenyl)-benzoic acid, 2-hydroxy-3-chloro-5-(3'-chloro-4'-fluorophenyl)-benzoic acid, 2-hydroxy-3-bromo-5-(3'-chloro-4'-fluorophenyl)-benzoic acid, 2-hydroxy-4-methyl-5-(2'-chloro-4'-fluorophenyl)-benzoic acid, 2-hydroxy-4-ethyl-5-(2'-chloro-4'-fluorophenyl)-benzoic acid, 2-hydroxy-4-benzyl-5-(2'-chloro-4'-fluorophenyl)-benzoic acid, 2-hydroxy-4-chloro-5-(2'-chloro-4'-fluorophenyl)-benzoic acid, and 2-hydroxy-4-bromo-5-(2'-chloro-4'-fluorophenyl)-benzoic acid, respectively.

Similarly, when 2-methyl-4-(4'-fluorophenyl)-phenol obtained from Example 6 is used in place of 4-(4'-fluorophenyl)-phenol in the above example, there is obtained 2-hydroxy-4-(4'-fluorophenyl)-3-methyl-benzoic acid.

EXAMPLE 8

Sodium-2-hydroxy-5-(4'-fluoro-2'-methoxyphenyl)-benzoate

A mixture of 0.1 mole of 2-hydroxy-5-(4'-fluoro-2'-methoxyphenyl)-benzoic acid and 0.1 mole of sodium hydroxide in 100 ml. of water is stirred at room temperature for one-half hour. The reaction mixture is then concentrated in vacuo to yield sodium-2-hydroxy-5-(4'-fluoro-2'-methoxyphenyl)-benzoate.

When the benzoic acid compounds obtained from Example 7 are used in place of the 2-hydroxy-5-(4'-fluoro-2'-methoxyphenyl)-benzoic acid in the above example, there are obtained the corresponding sodium salts.

Similarly, when choline, glucosamine, S-methylmethionine, potassium hydroxide, ammonium hydroxide, barium hydroxide, calcium hydroxide, piperazine, chloroquine, hydroxychloroquine, dimethylaminoethanol, and magnesium hydroxide, are used in place of sodium hydroxide in the above example, there are obtained the corresponding choline, glucosamine, S-methyl-methionine, potassium, ammonium, barium, calcium, piperazine, chloroquine, hydroxychloroquine, dimethylaminoethanol and magnesium salts, respectively.

EXAMPLE 9

Methyl-2-hydroxy-5-(4'-fluoro-2'-methoxyphenyl)-benzoate

A solution of 5.0 grams of 2-hydroxy-5-(4'-fluorophenyl)-benzoic acid in 20 ml. of methanol and 2 ml. of concentrated sulfuric acid is heated at reflux for 5 hours. The mixture is then cooled and partitioned between (75:150 ml.) water and ethyl acetate and the organic layer washed with dilute sodium bicarbonate solution. The organic layer is then dried over magnesium sulfate and concentrated in vacuo to yield approximately 5.0 grams of methyl-2-hydroxy-5-(4'-fluoro-2'-methoxyphenyl)-benzoate.

When the benzoic acid compounds obtained from Example 7 are used in place of 2-hydroxy-5-(4'-fluoro-2'-methoxyphenyl)-benzoic acid in the above example, there are obtained the corresponding methyl esters.

Similarly, when ethanol and n-butanol are used in place of methanol in the above example, there are obtained the corresponding methyl and n-butyl esters.

EXAMPLE 10

1,3-bis-[5'-4''-Fluorophenyl)-2'-acetoxy-benzoyloxy)-propane

A mixture of 0.1 mole of 2-acetoxy-5-(4-fluorophenyl)-benzoic acid and 0.15 mole of thionyl chloride is heated at reflux until evolution of hydrogen chloride has practically ceased. Excess thionyl chloride is removed in vacuo. To a solution of the resulting crude acid chloride in 100 ml. of pyridine is added 0.05 mole of propane-1,3-diol. After standing at 25° C. for 24 hours, the pyridine is removed in vacuo at a temperature lower than 40° C., and the residual product is taken up in benzene, washed with dilute hydrochloric acid, dilute sodium bicarbonate, and the product chromatographed on a column of silica gel. Elution with benzene containing increasing proportions of acetone furnishes 1,3-bis-[5'-(4''-fluorophenyl)-2'-acetoxy-benzoyloxy]-propane.

Alternatively, the reaction may be carried out by reacting at room temperature for 5 hours a mixture of 0.1 mole of 2-acetoxy-5-(4'-fluorophenyl)-benzoic acid, 0.1 mole of dicyclohexylcarbiodiimide and 0.1 mole of propane-1,3-diol in 20 parts of tetrahydrofuran. After the reaction, the mixture is filtered and the filtrate concentrated, dissolved in ether and washed with aqueous sodium bicarbonate. The ether solution is then dried over sodium sulfate and concentrated to yield the desired product.

When β-ethoxyethanol, benzyl alcohol, phenol, p-acetylaminophenol, 4-methoxyphenol, 4-dimethylaminophenol, methyl 2-hydroxybenzoate, benzyl-2-hydroxy-5-(4'-fluorophenyl)-benzoate β-dimethylaminoethanol, or β-diethylaminopropanol benzyl-2-hydroxybenzoate is used in place of 1,3-propane diol in the above example, there is obtained the corresponding 2-ethoxyethane, toluene, benzene, p-acetylaminobenzene, 4-methoxybenzene, 4-dimethylaminobenzene, 2-carbomethoxybenzene, 2-carbobenzyloxy-5-(4'-fluorophenyl)-benzene, β-dimethylaminoethylbenzene, β-diethylaminopropyl-benzene, and 2-carbobenzyloxybenzene compounds, respectively.

EXAMPLE 11

Phenyl-2-acetoxy-5-(4'-fluoro-2'-methoxyphenyl)benzoate

A mixture of 2-acetoxy-5-(4'-fluoro-2'-methoxyphenyl)-benzoic acid (0.1 mole), phosphorous oxychloride (0.1 mole), and phenol (0.12 mole), is heated at 75° C. until no more hydrogen chloride is evolved. The product, phenyl-2-acetoxy-5-(4'-fluoro-2'-methoxyphenyl)-benzoate, is isolated by partitioning the reaction mixture between benzene and dilute sodium bicarbonate solution, and subjecting the benzene solution to chromatography on silica gel.

By substituting other phenolic compounds in the foregoing example, e.g. p-methoxyphenol, p-dimethylaminophenol, or p-acetaminophenol, the corresponding substituted phenyl esters, e.g. p-methoxyphenyl, p-dimethylaminophenyl, or p-acetaminophenyl-2-acetoxy-5-(4'-fluoro-2'-methoxyphenyl)-benzoic acid are obtained.

EXAMPLE 12

2-Hydroxy-5-(4'-fluorophenyl)-benzamide

A mixture of 5.3 grams of methyl-2-hydroxy-5-(4'-fluorophenyl)-benzoate and 20 ml. of liquid ammonia is reacted in a bomb at 100° C. for 4 hours. After cooling the bomb is opened and the ammonia allowed to evaporate. The residue is then recrystallized from benzene to yield 2-hydroxy-5-(4'-fluorophenyl)-benzamide (m.p. 206° - 207° C.).

When the benzoic acid methyl esters obtained from Example 9 are used in place of methyl-2-hydroxy-5-(4'-fluorophenyl)-benzoate in the above example, there are obtained the corresponding benzamide compounds.

Similarly, when methylamine, diethylamine, β-dimethylaminoethylamine, hydrazine, hydroxylamine, morpholine, N-ethylpiperidine, N-(β-hydroxyethyl)-piperidine, or β-hydroxyethylamine are used in place of ammonia in the above example, there are obtained the corresponding N-methylamide, N-diethylamide, N-(β-dimethylaminoethyl)-amide, hydrazide, N-hydroxyamide, morpholide, 4-ethylpiperidide, 4-(β-hydroxyethyl)-piperidide, or β-hydroxylethylamide, respectively.

EXAMPLE 13

N-[2-Hydroxy-5-(4'-fluorophenyl)-benzoyl]-glycine

To a solution of 10 mmole of 2-acetoxy-5-(4'-fluorophenyl)-benzoic acid and 10 mmole of triethylamine in 25 ml. of dioxane and 5 ml. of acetone at 0° - 5° C. is added 10 mmole of isobutylchlorocarbonate. After the mixture has been stirred at 0° - 5° C. for 1 hour, a solution of 10 mmole of methyl glycinate in 6 ml. of water and 10 mmole of triethylamine is added, and the stirring continued for another hour. After the addition of 75 ml. of water, the mixture is extracted with ether. The ether solution is washed successively with cold 1 N hydrochloric acid, and cold saturated sodium bicarbonate solution, then dried over sodium sulfate, and evaporated. The residual material is saponified by treatment with 10 ml. of 2.5 N sodium hydroxide solution in 25 ml. of methanol for 0.5 hour. The methanol is removed by distillation in vacuo and the remaining aqueous solution is extracted with ether and the acidified with dilute hydrochloric acid. The product is filtered, washed, and dried. Recrystallization from benzene-hexane results in purification of the material.

By applying a similar process to the esters of other amino acids, suitably protected as needed, such as alanine, phenylaline, tyrosine, taurine, and the like, the corresponding substituted amino acids are obtained.

EXAMPLE 14

2-Acetoxy-5-(4'-fluorophenyl)-benzoic acid

A solution of 3.0 grams of 2-hydroxy-5-(4'-fluorophenyl)-benzoic acid in 12 ml. of pyridine and 8 ml. of acetic anhydride is heated on a steam bath for 20 minutes. The mixture is then poured onto ice and the product extracted with methylene chloride. The methylene chloride solution is dried and then evaporated. The residue is recrystallized from benzene to yield 2-acetoxy 5-(4'-fluorophenyl)-benzoic acid (m.p. 134° – 137° C.).

When the 2-hydroxy-benzoic acid compounds obtaied from Example 7 are used in place of 2-hydroxy-5-(4'-fluorophenyl)-benzoic acid in the above example, there are obtained the corresponding 2-acetoxy-benzoic acid compounds.

Similarly, when propionic acid anhydride is used in place of acetic anhydride, the corresponding 2-propionoxy compound is obtained.

EXAMPLE 15

2-Allyloxy-5-(4'-fluorophenyl)-benzoic acid

To a solution of 0.1 mole of methyl-2-hydroxy-4-(4'-fluorophenyl)-benzoate in 400 ml. of methanol is added 0.1 mole of sodium methoxide, followed by addition of 0.1 mole of allyl chloride. This mixture is then heated at reflux for 4½ hours. The reaction mixture is then cooled, filtered, and concentrated in vacuo to an oil, filtered again, and distilled in vacuo to obtain methyl2-allyloxy-5-(4'-fluorophenyl)-benzoate. This ester is then saponified by heating with ethanolic aqueous potassium hydroxide to obtain the corresponding potassium salt. This solution is then acidified with 2½ N aqueous hydrochloric acid and the reaction mixture concentrated in vacuo to yield 2-allyloxy-5-(4'-fluorophenyl)-benzoic acid.

When the 2-hydroxy-benzoate compounds obtained from Example 9 are used in place of methyl-2-hydroxy-5-(4'-fluorophenyl)-benzoate in the above example, there are obtained the corresponding allyloxy-benzoic acid compounds.

Similarly, when 2-butenyl chloride is used in place of allyl chloride in the above example, there is obtained the corresponding 2-(2''-butenyloxy) compound.

EXAMPLE 16

2-Methoxy-5-(4'-fluorophenyl)-benzoic acid

A solution of 0.1 mole of methyl-2-hydroxy-5-(4'-fluorophenyl)-benzoate in 100 ml. of acetone is treated with 20 grams of potassium carbonate and 0.1 mole of dimethyl sulfate. The mixture is then heated at reflux for 3 hours. After cooling, the solvent is removed by distillation, and the mixture is made barely acid with dilute aqueous hydrochloric acid. The reaction mixture is then extracted with methylene chloride and chromatographed on a silica gel column using petroleum benzinether as eluent. The 2-methoxy-benzoate thus obtained is saponified by heating with dilute aqueous potassium hydroxide. The saponified reaction mixture is then made slightly acid with dilute aqueous hydrochloric acid and then concentrated in vacuo to yield 2-methoxy-5-(4'-fluorophenyl)-benzoic acid.

When the 2-hydroxy-benzoate compounds obtained from Example 9 are used in place of methyl-2-hydroxy-5-(4'-fluorophenyl)-benzoate in the above example, there are obtained the corresponding 2-methoxy-benzoate compounds.

Similarly, when diethyl sulfate or butyl tosylate are used in place of dimethyl sulfate in the above example, there are obtained the corresponding ethoxy or butoxy benzoic acid compounds.

EXAMPLE 17

Anhydride of 2-acetoxy-4-(4'-fluoro-2'-methoxyphenyl)benzoic acid

A solution of 0.01 mole of 2-acetoxy-4-(4'-fluoro-2'-methoxyphenyl)-benzoic acid and 0.01 mole of thionyl chloride in 30 ml. of dry benzene is warmed until the formation of the substituted benzoyl chloride is complete. The resulting solution is concentrated to one-half volume in vacuo and is added to a solution of 0.01 mole of 2-acetoxy-4-(4'-fluoro-2'-methoxyphenyl)benzoic acid and 0.01 mole of pyridine in 30 ml of benzene. The mixture is stirred at room temperature overnight, filtered, and the filtrate washed with cold dilute sodium bicarbonate solution. After drying and removal of benzene, the product is recrystallised from benzene-hexane.

Alternatively, the anhydride may be formed by reacting for 5 hours at room temperature 0.02 mole of 2-acetoxy-4-(4'-fluoro-2'-methoxyphenyl)-benzoic acid and 0.01 mole of dicyclohexylcarbodiimide in 20 parts of tetrahydrofuran, followed by filtration and concentration of the filtrate to yield the anhydride.

When a solution of 2-acetoxy benzoic acid in pyridine is used in place of the 2-acetoxy-4-(4'-fluoro2'-methoxyphenyl)-benzoic acid pyridine solution in the above example, there is obtained the mixed anhydride of 2-acetoxy-4-(4'-fluoro-2'-methoxyphenyl)-benzoic acid and 2-acetoxy benzoic acid.

EXAMPLE 18

[2''-Carboxy-4''-(4'''-fluorophenyl)]-phenyl-2-acetoxy-5-(4'-fluorophenyl)-benzoate 0.01 Mole of [2''-carbobenzyloxy-4''-(4'''-fluorophenyl)]-phenyl-2-acetoxy-5-(4'-fluorophenyl)-benzoate in 50 ml. of ethanol is hydrogenated in the presence of 10% palladium-on-charcoal until an equivalent amount of hydrogen is absorbed. The reaction mixture is then filtered and the filtrate concentrated in vacuo. The concentrate is then recrystallized from aqueous ethanol.

When the 2-carbobenzyloxy-benzene compound obtained from Example 10 is used in place of the benzoate in the above example, there is obtained the corresponding 2-carboxy compound.

EXAMPLE 19

3-Allyl-5-(4'-fluorophenyl)-2-hydroxy-benzoic acid

A. Methyl-2-allyloxy-5-(4'-fluorophenyl)-benzoate

A mixture of 6.6 g. of methyl-5-(4'-fluorophenyl)-2-hydroxy-benzoate, 5.5 g. of potassium carbonate, 25 ml. of acetone, and 4.5 g. of allyl bromide is heated at reflux for 2 hours, and then stirred at 25° C. overnight. The reaction mixture is partitioned between 100 ml. of water and 100 ml. of ether, the ether solution is dried over magnesium sulfate and concentrated to a thick oil, 6.0 g.

This material shows a strong absorption band in the infra-red at 5.75 μ (non-bonded ester) and is homogeneous by thin layer chromatography.

B. Methyl-3-allyl-5-(4'-fluorophenyl)-2-hydroxy-benzoate

A sample of methyl-2-allyloxy-5-(4'-fluorophenyl)-benzoate is heated under a nitrogen atmosphere at 235° C. for 35 minutes. The crude product, which solidifies on cooling, is recrystallized from ethanol to obtain methyl-3-allyl-5-(4'-fluorophenyl)-2-hydroxybenzoate, m.p. 76° – 77° C.

C. 3-Allyl-5-(4'-fluorophenyl)-2-hydroxy-benzoic acid

A mixture of 3.9 g. methyl-3-allyl-5-(4'-fluorophenyl)-salicylate, 40 ml. of methanol, and 10 ml. of 2.5 N sodium hydroxide solution is heated at reflux for 15 minutes. The mixture is concentrated in vacuo to remove methanol, diluted to 60 ml. with water, and acidified with dilute hydrochloric acid. The product is collected by filtration, dried, and recrystallized from benzene. The yield of 3-allyl-5-(4'-fluorophenyl)-2-hydroxy-benzoic acid is 3.4 g., m.p. 170° – 172° C.

When the 3-unsubstituted ester compounds of Examples 9, 10 and 11 are used in place of methyl-5-(4'-fluorophenyl)-2-hydroxy-benzoate in the above example, there are obtained the corresponding 3-allyl-benzoic acid compounds.

EXAMPLE 20

3-Propyl-5-(4'-fluorophenyl)-2-hydroxy-benzoic acid

A solution of 0.8 g. of 3-allyl-5-(4'-fluorophenyl)-2-hydroxy-benzoic acid in 25 ml. of ethanol is subjected to hydrogenation at 40 p.s.i. and 25° C. in the presence of 0.1 g. of platinum oxide. After the uptake of the required amount of hydrogen, the catalyst and solvent are removed, and the crude product is recrystallized from benzene. The yield of 3-propyl-5-(4'-fluorophenyl)-2-hydroxy-benzoic acid is 0.72 g., m.p. 188°14 190° C.

When the 3-allyl-benzoic acid compounds obtained from Example 14 are used in place of 3-allyl-5-(4'-fluorophenyl)-2-hydroxy-benzoic acid in the above example, there are obtained the corresponding 3-propyl-benzoic acid compounds.

EXAMPLE 21

3-Propenyl-5-(4'-fluorophenyl)-2-hydroxy-benzoic acid

A mixture of 2 g. of 3-allyl-5-(4'-fluorophenyl)2-hydroxy-benzoic acid, 5 g. of potassium hydroxide pellets and 2 ml. of water was heated under nitrogen in an oil bath at 170° C. for 1 hour with occasional stirring. The reaction mixture was cooled, dissolved in water, and the solution acidified. The product was extracted into ether. After drying the ether solution, and removing the ether, the product was recrystallized from benzene to yield 1.37 g., m.p. 196° –200° C. One more recrystallization from benzene raised the m.p. to 198° –201° C.

When the 3-allyl-benzoic acid compounds obtained from Example 19 are used in place of 3-allyl-5-(4'-fluorophenyl)-2-hydroxy-benzoic acid in the above example, there are obtained the corresponding 3-propenyl-benzoic acid compounds.

EXAMPLE 22

A dry filled capsule was prepared from the following components:
2-hydroxy-5-(2' -methoxy-4'-fluorophenyl)
benzoic acid: 300 mg.
corn starch: 150 m.g.
Cab-o-sil: 5 m.g.
Sterotex: 15 m.g.

A dry filled capsule can be prepared by using the following compounds as active ingredients instead of 2-hydroxy-5-(2'-methoxy-4'-fluoropheny)-benzoic acid:
2-hydroxy-5-(4'-fluorophenyl)-benzamide;
2-acetoxy-5-(4'-fluorophenyl)-benzamide;
2-acetoxy-5-(4'-fluorophenyl)-3-methyl benzamide;
2-hydroxy-5-(2'-methoxy-4'-fluorophenyl)-benzoic acid;
2-hydroxy-5-(2'methyl-4'-fluorophenyl)-benzoic acid;
2-hydroxy-5-(3'-methyl-4'-fluorophenyl)-benzoic acid;
or any other preferred compounds as shown in the specification.

If capsules of lower potency are to be made, the capsule size could be reduced or the quantity of corn starch could be increased.

EXAMPLE 23

Compressed tablets were prepared with the following components:
2-hydroxy-5-(2'-methoxy-4'-fluorophenyl) benzoic acid: 300 m.g.
corn starch: 30 m.g.
polyvinylpyrrolidone: 10 m.g.
magnesium stearate: 3 m.g.

Tablets as above can be prepared by using the following compounds as active ingredients instead of 2-hydroxy-5-(2'-methoxy-4'-fluorophenyl)-benzoic acid:
2-hydroxy-5-(4'-fluorophenyl)-benzamide;
2-acetoxy-5-(4'-fluorophenyl)-benzamide;
2-acetoxy-5-(4'-fluorophenyl)-3-methyl benzamide;
2-hydroxy-5-(2'-methoxy-4'-fluorophenyl)-benzoic acid;
2-hydroxy-5-(2'-methyl-4'-fluorophenyl)-benzoic acid;
2-hydroxy-5-(3'-methyl-4'-fluorophenyl)-benzoic acid;
or any other especially preferred compounds as shown in the specification.

Tablets of other potencies would be made of altering the tablet size as necessary.

We claim:
1. A compound of the formula:

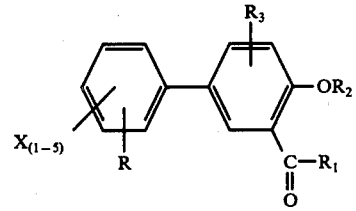

wherein
X is halogen;
R is
halogen,
lower alkyl, or
lower alkoxy;
$R_1$ is
amino,
loweralkylamino,
diloweralkylamino, diloweralkylaminoloweralkylamino,
hydrazino,
hydroxylamino,
N-morpholino,
N-(4-loweralkylpiperidino),
N-[4-hydroxyloweralkyl)-piperidino], or
hydroxyloweralkylamino;

$R_2$ is
   hydrogen, or
   loweralkanoyl; and $R_3$ is
   hydrogen,
   lower alkyl,
   lower alkoxy,
   benzyl,
   lower alkenyl or
   halo.

2. A compound of the formula:

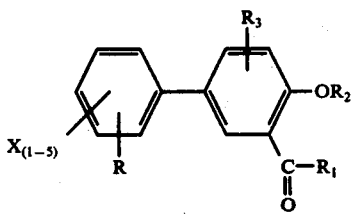

wherein
   X is chloro or fluoro;
   R is hydrogen, lower alkyl, or lower alkoxy;
   $R_1$ is amino,
   $R_2$ hydrogen or lower alkanoyl; and
   $R_3$ is lower alkyl or hydrogen.

3. A compound of claim 2 wherein:
   R is hydrogen;
   $R_1$ is amino;
   $R_2$ is hydrogen;
   $R_3$ is hydrogen; and
   X is fluoro and is the 4'-position, thus forming 2-hydroxy-5-(4'-fluorophenyl)-benzamide.

4. A compound of claim 2 wherein:
   R is hydrogen;
   $R_1$ is amino;
   $R_2$ is acetyl;
   $R_3$ is hydrogen; and
   X is fluoro and is in the 4'-position, thus forming 2-acetoxy-5-(4'-fluorophenyl)-benzamide.

5. A compound of claim 2 wherein:
   R is hydrogen;
   $R_1$ is amino;
   $R_2$ is acetyl;
   $R_3$ is methyl and is in the 3-position;
   X is fluoro and is in the 4'-position, thus forming 2-acetoxy-5-(4'-fluorophenyl)-3-methylbenzamide.

* * * * *